United States Patent
Slusarewicz

(10) Patent No.: US 6,773,462 B2
(45) Date of Patent: Aug. 10, 2004

(54) METHOD OF COLORING HAIR

(75) Inventor: Pawel Slusarewicz, Irvington, NY (US)

(73) Assignee: Unilever Home & Personal Care USA Division of Conopco, Inc., Chicago, IL (US)

(*) Notice: Subject to any disclaimer, the term of this patent is extended or adjusted under 35 U.S.C. 154(b) by 216 days.

(21) Appl. No.: 10/117,640

(22) Filed: Apr. 5, 2002

(65) Prior Publication Data
US 2002/0197224 A1 Dec. 26, 2002

(30) Foreign Application Priority Data
Apr. 6, 2001 (GB) .............................. 0108735

(51) Int. Cl.$^7$ ................................. A61K 7/13
(52) U.S. Cl. ................ 8/401; 8/405; 8/428; 8/432; 8/493; 8/587; 8/618
(58) Field of Search ................ 8/401, 405, 428, 8/432, 493, 587, 618

(56) References Cited

U.S. PATENT DOCUMENTS 5,490,980 A * 2/1996 Richardson et al. ........ 424/94.6
5,525,336 A   6/1996 Green et al. ............... 424/94.5

FOREIGN PATENT DOCUMENTS

DE   199 45 486 A   3/2001
WO   99/36570       7/1999
WO   00/64405      11/2000

OTHER PUBLICATIONS

Copending application: Applicant: Slusarewicz Serial No.: 10/117,404 Case No: J3598(C) Filed: Apr. 5, 2002 For: Hair Coloring Compositions.

International Search Report Application No. PCT/EP 02/03927 mailed Aug. 5, 2002.

Gardner J. M. et al. "Investigation into the Action of Transglutaminase on Human Hair", Journal of the Society Cosmetic Chemists, vol. 46, No. 1.2/95, pp. 11–28, XP000929527.

* cited by examiner

Primary Examiner—Brian P. Mruk
Assistant Examiner—Eisa Elhilo
(74) Attorney, Agent, or Firm—Michael P. Aronson

(57) ABSTRACT

A method of coloring hair comprises: treating hair with an oxidizing agent; and applying to the hair either during or after treatment with the oxidizing agent a composition comprising a compound which is capable of acting as a substrate for endogenous transglutaminase in and/or on the hair and which comprises a chromophore that is capable of absorbing and/or emitting light in the visible part of the electromagnetic spectrum. Products for use in the method comprise the oxidizing agent packaged separately from the compound.

15 Claims, No Drawings

METHOD OF COLORING HAIR

FIELD OF THE INVENTION

This invention relates to a method of colouring hair and to hair colouring products.

BACKGROUND OF THE INVENTION

The cosmetic colouring of hair has been known for many years. Colourants are typically classified as being temporary or permanent. In temporary colouring, the colour can be washed from the hair relatively easily. So-called permanent colouring of hair typically involves the formation of oligomeric or polymeric compounds in and/or on the hair fibre. However, the colouring is not truly permanent in the strict sense of the word because the colourants can still be washed from the hair over longer periods of time.

Therefore, there remains a need for hair colourants which are more resistant to being washed off the hair.

It is known that hair fibres contain certain enzymes in and/or on the fibre. For example, the enzyme transglutaminase has been found to be present in hair fibres. Transglutaminase catalyses the formation of covalent bonds between specific peptide-bound glutamine resides and various primary amino groups of peptide-bound lysines or polyamines, acting as aminic donor substrates.

Transglutaminase can be utilised to attach agents to body tissues, as described in WO99/36570. In the specific systems exemplified in this document, exogenous transgutaminase is used to attach polylysine or polyglutamine to skin or hair. In the only specific example of a system for application to hair, a mousse for thickening hair is described which contains a mucopolysaccharide linked to polyglutamine.

Transglutaminase substrates have been involved in the treatment of hair loss. For example, FR-A-2740331 describes cosmetic compositions for the treatment of hair which contain one or more esters of butyric acid and, optionally, a substrate for transglutaminase.

The use of exogenous transglutaminase in a cosmetic composition for forming a protective layer on the hair, skin or nails, is described in U.S. Pat. No. 5,525,336. The ingredients of the composition cross-link with the outer layer of skin, hair or nails to form the layer.

WO00/64405 describes the use of substrates for a variety of endogenous enzymes that are present in hair fibres, for the delivery of hair benefit agents to the hair.

Transglutaminase is one of the endogenous enzymes mentioned in the document.

It is well-known that hair can be treated with bleaching agents, such as hydrogen peroxide. The bleaching agents generally act either to decolourise the hair or they act on dye precursor compounds to form coloured compounds on the hair. Hair contains the pigment melanin in granular form within the hair cortex. The darker the perceived hair colour, the higher the concentration of melanin in the hair. The objective of hair bleaching compositions is to decolourise both the naturally occurring melanin pigment and in addition any synthetic pigments applied to the hair.

The present invention is based on the finding of specific systems for colouring hair which may involve the action of endogenous transglutaminase. The systems have the advantage in that the colourant may be covalently bound to the hair fibre and, therefore, more resistant to being removed by washing. The systems have the further advantage that they can involve a milder method for the treatment of hair which requires a single bleaching step only. The invention involves the recognition that, surprisingly, pretreatment of the hair with an oxidising agent serves to enhance the binding of a dye to the hair by means of transglutaminase, even though the transglutaminase enzyme, which is known to be sensitive to oxidation, would have been expected to be inactive or to have reduced activity on hair treated with an oxidising agent.

SUMMARY OF THE INVENTION

According to a first aspect of the present invention, there is provided a method of colouring hair which comprises:

treating hair with an oxidising agent; and applying to the hair either during or after treatment with the oxidising agent a composition comprising a compound which is capable of acting as a substrate for endogenous transglutaminase in and/or on the hair and which comprises a chromophore that is capable of absorbing and/or emitting light in the visible part of the electromagnetic spectrum.

In a second aspect, the invention provides a hair colouring product in the form of a kit of parts comprising a hair oxidising agent packaged separately from a composition comprising a compound which is capable of acting as a substrate for endogenous transglutaminase in and/or on the hair and which comprises a chromophore that is capable of absorbing and/or emitting light in the visible part of the electromagnetic spectrum.

DETAILED DESCRIPTION OF THE INVENTION

The present invention is based on the finding of particularly effective methods and products for colouring hair. The methods and products involve the use of a compound which can act as a substrate for transglutaminase. The compound preferably forms a covalent bond to the hair by the action of the endogenous transglutaminase in and/or on the hair. The method of the invention involves treating hair with an oxidizing agent either before or during treatment with the compound.

Compound which is Capable of Active as a Substrate for Endogenous Transglutaminase The compound which is capable of acting as a substrate for endogenous transglutaminase in and/or on hair and which comprises a chromophore that is capable of absorbing and/or emitting light in the visible part of the electromagnetic spectrum (also referred to herein as the compound) preferably comprises an amino group covalently bonded to the chromophore.

In a preferred embodiment, the compound comprises a group of formula $NH_2$ covalently bonded to the chromophore by a linker group of formula $(CH_2)_n$, wherein n is an integer from 1 to 12, more preferably from 1 to 6, most preferably from 3 to 5. Optionally, the linker group can contain one or more other atoms in the $(CH_2)_n$ chain, such as, for example, O. These compounds are known to be suitable as substrates for transglutaminase. The precise nature of the linker group is not critical, provided that the compound can act as a substrate for transglutaminase. Suitable methods for attaching the amino group to the chromophore via the linker group are well-known in the art. Alternatively, the compound may be synthesised or otherwise obtained with the amino and linker groups already present in the chromophore. The compound may contain one or more than one amino group and/or more than one chromophore.

The compound may be used in the method of the invention in solution. Preferably, the solution will be aqueous, containing as solvent from 50 to 100% water. However, other cosmetically acceptable solvents and/or diluents may be present in the solution such as, for example, ethanol and/or other lower alcohols. When the compound is present in solution, it will typically be present in the solution at a concentration of from 0.0001M to 0.01M, although the concentration may fall outside this range and will depend on the particular product form.

The nature of the chromophore in the compound can vary widely, provided that, when the compound is bonded to the hair, the hair is coloured by the compound. Therefore, the chromophore can be inorganic (ie, metal ion based) or organic. Preferably, however, the chromophore in the compound is an organic dye. Suitable organic dyes are well-known in the art and may comprise a plurality of ring systems, at least some of which are aromatic, and one or more groups bearing a positive or negative charge.

Although the dye may impart any colour to the hair, the compounds of the invention have been found to be particularly effective at colouring the hair red. Permanent red colouration of hair is difficult to achieve using conventional hair colouring techniques.

The methods and products of the invention may comprise a single compound or a mixture of different compounds, for example having the same or different light absorbing and/or emitting properties.

The Oxidising Agent

The methods and products of the invention involve the use of at least one oxidising agent. The oxidising agent is suitable for cosmetic application to hair at the concentration used in the invention. Preferably, the oxidising agent is a peroxygen compound, such as of the type conventionally used for bleaching hair or for colouring hair (when a dye precursor compound is also used). Mixtures of two or more such compounds may be used if desired.

Hydrogen peroxide is the most preferred peroxygen compound for use in the systems of the present invention, though many other peroxygen compounds are suitable.

Other peroxygen compounds suitable for use are generally water soluble peroxygen compounds such as peroxygen bleaches capable of yielding hydrogen peroxide in aqueous solution. Water soluble in this respect means a peroxygen compound which can be substantially solubilised in water at 25° C. Water soluble peroxygen bleaching compounds are well known in the art and, other than hydrogen peroxide, include inorganic alkali metal peroxides such as sodium periodate and sodium peroxide, organic peroxides such as urea peroxide and melamine peroxide and inorganic perhydrate salt bleaching compounds such as the alkali metal salts of perborates, percarbonates, perphosphates, persilicates, persulphates and the like.

The peroxygen compound is generally used in the methods and products of the present invention as an aqueous solution containing the peroxygen compound at a level from 0.01% to 40%, preferably from 0.1% to 20%, most preferably from 1% to 7%, by weight.

The Reducing Agent

In the methods and products of the invention, the compound is optionally applied to the hair together with a reducing agent. The reducing agent preferably comprises one or more thiol (SH) groups. Compounds containing thiol groups are known in other applications to be cosmetically acceptable for application to the hair.

Suitable reducing agents include, for example, compounds containing from 1 to 6 carbon atoms and one or more other functional groups such as hydroxyl and carboxylate, eg, dithiothreitol, thioglycolate and mixtures thereof.

A non-exausitive list of reducing agents is as follows: Mercapto-carboxylic Acids (e.g. 2-mercaptopropionic acid, 3-mercaptopropionic acid, mercaptosuccinic acid, thioglycolic acid, ammonium thioglycollate, sodium thioglycollate, L-cysteine, Di-mercapto-adipic acid); Mercapto-amines (e.g. L-cysteine, ethyl ester, L-cysteine methyl ester, N-acetyl-L-cysteine, cysteamine); Mercapto-amides (e.g. thioglycolamide, N-hydroxyethyl mercapto-acetamide, N-methyl mercapto acetamide, 2-mercapto-propionamide); Sulphites (e.g. ammonium bisulphite, sodium bisulphite, ammonium sulphite, sodium sulphite); hydroxides (e.g. guanidine hydroxide, sodium hydroxide); Alcohols and Diols (e.g. resorcinol, thioglycerol, glycerol monothioglycollate, glycol thioglycolate); Di-thio compounds (e.g. dihydrolipoic acid, sodium dihydrolipoate, dithiothreitol, 1,3-dithiopropanol); Others (e.g. lithium chloride, tris(hydroxymethyl)phosphine, cuprar.-monium hydroxide, thioglycolic hydrazide, 2-mercapto-ethanesulphonic acid, homocysteine thiolactone, polythiol polymers, salts of hydrogen sulphide, amines in alkaline solution, salts of hydrogen cyanide, borohydride, dithionite, ester salts of sulphoxylate).

The reducing agent is typically used in the methods and products of the invention in solution. Preferably, the solution will be aqueous, containing as solvent from 50 to 100% water. However, other cosmetically acceptable solvents and/ or diluents may be present in the solution such as, for example, ethanol and/or other lower alcohols. When the reducing agent is in solution, it is preferably used in an amount such that the molar ratio of the reducing agent to the compound is in the range of from 10:1 to 1:1.

It is surprising that the method of the invention is effective given that it can involve both an oxidising agent and a reducing agent which might reasonably have been expected to operate by opposite mechanisms.

Compositions of the Invention

In the methods and products of the invention, the compositions that are applied to the hair preferably have a pH of from about 7.5 to about 9.5, more preferably from about 8 to about 9. It has been found that compositions having pH values within this range are particularly effective at colouring hair. The pH can be maintained within this range by the use of suitable buffering agents. Suitable buffering agents are conventional in the art.

Hair Colouring Agents

The compositions of the methods and products of the present invention optionally additionally include one or more conventional hair colouring agents. Hair colouring agents suitable for use in the compositions of the present invention include non-oxidative dyes. Such hair colouring agents may be used with the compositions of the present invention to formulate compositions which have suitable colours and which retain the colour over a period of time.

Non-oxidative dyes include direct dyes, semi-permanent, temporary and other dyes. Various types of non-oxidative dyes are well known in the art.

Natural dyes and vegetable dyes may also be included in the colouring compositions of the present invention.

Examples include henna, camomile, indigo, logwood and walnut hull extract.

Temporary hair dyes, or hair colouring rinses, are generally comprised of dye molecules which are too large to diffuse into the hair shaft and which act on the exterior of the hair. They are usually applied via a leave-in procedure in which the dye solution is allowed to dry on the hair surface.

Semi-permanent hair dyes are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process. Suitable semi-permanent dyes for use in the compositions of the present invention include HC Blue 2, HC Yellow 4, HC Red 3, Disperse Violet 4, Disperse Black 9, HC Blue 7, HC Yellow 2, Disperse Blue 3, Disperse violet I and mixtures thereof.

Direct dyes, such as nitro dyes do not require oxidation to dye the hair. They are usually applied to the hair in a base formulation which includes surfactant material. Suitable direct dyes include derivatives of nitroamino benzene, nitro aryl amines or azo dyes.

Optional Materials and Cosmetic Adjunct

Besides the actives, the compositions of the present invention may also contain other ingredients conventionally used in the art such as diluents, sequestrants, thickeners, carriers, surfactants (anionic, cationic, nonionic, amphoteric, zwitterionic and mixtures thereof), antioxidants, proteins, polypeptides, preservatives, moisturising agents, solvents, perfumes, enzymes, polymers and conditioners.

The compositions of the invention may comprise a source of calcium ions (for example a soluble inorganic calcium salt). Calcium ions may assist the action of the transglutaminase enzyme. However, a source of calcium ions is not essential because, due to the presence of calcium from other sources (for example in local water), sufficient calcium ions may already be present.

The compositions may contain exogenous transglutaminase in order to assist in binding of the hair fibre to the compound. However, the invention can work effectively without exogenous transglutaminase, relying solely on transglutaminase in and/or on the hair. Therefore, the compositions of the invention are preferably free or substantially free of exogenous transglutaminase.

Compositions of the invention may optionally contain hair penetration agents. Hair penetration agents assist the penetration of molecules into the hair fibre and are conventionally used for this purpose. Suitable hair penetration agents include, for example, compounds comprising amino and/or amide groups such as urea and guanidine, for example. The reducing agent which is used in the compositions of the invention may also act as a hair penetration agent.

Product Form

The products according to the present invention are presented in the form of a kit of parts comprising multiple containers or a single container having multiple compartments.

One component of the kit comprises a compound which is capable of acting as a substrate for endogenous transglutaminase in and/or on hair and which comprises a chromophore that is capable of absorbing and/or emitting light in the visible part of the electromagnetic spectrum, individually packaged. A further kit component comprises an individually packaged oxidising agent. In one embodiment of the present invention the individually packaged oxidising agent comprises a stabilised aqueous solution of a water-soluble peroxygen bleach compound, most generally hydrogen peroxide in an amount such that the final concentration of the compound for use on the hair is from 0.5% to 14% by weight of the composition. Optional ingredients may be incorporated into either component, generally depending on their stability in the different components which can be readily determined by the skilled person.

The compartmentalised ingredients of the product are generally used separately from each other, with the part of the product that comprises the oxidising agent being applied to the hair first, followed by the part of the product comprising the compound. Alternatively, the two parts of the product may be mixed by the user immediately prior to application to the hair.

Method of Use

The products and methods of the present invention may be used to colour hair. The products may be intended solely for colouring hair for use in a method dedicated to hair colouring. In such methods, the colouring products herein are applied to the hair for periods of from 1 minute to 90 minutes depending upon the degree of colouring required. Preferably, the hair, optionally washed and rinsed before the treatment, is treated with the hair oxidising agent for periods of from 1 minute to 90 minutes, optionally rinsed and then treated with the composition comprising the compound for periods of from 1 minute to 90 minutes. A preferred time for both treatment steps is between 5 minutes and 30 minutes. Hair is typically rinsed, optionally washed, and dried after such treatment. Elevated temperatures (eg, from 35 to 50° C.) may be employed at any stage of the treatment process.

The method of the invention may be applied to unpigmented hair eg, white or grey hair. The method may also be used to colour hair which is naturally pigmented or otherwise coloured (eg, by an earlier dyeing step). Transglutaminase has been found to be present in pigmented and unpigmented hair.

The invention will now be described, by way of non-limiting example only, with reference to the following examples. In the examples and throughout this specification, all references to percentages are to percentages by weight unless indicated otherwise.

EXAMPLES

Example 1

Materials and Methods

Procurement of Hair Fibres

Virgin blonde hair, defined as hair not previously exposed to any type of chemical treatment, was obtained from International Hair Importers Inc. as 500 g batches. The hair fibres were then made into 0.75 g, 5 cm length switches which were secured by a cable tie and Araldite® adhesive at one end.

Bleaching of Hair Switches

Hair switches were bleached with either peroxide (less harsh) or persulphate (more harsh). Peroxide bleaching solution was freshly made prior to use and contained 6.8 mM EDTA, 1.18 M hydrogen peroxide and 2 M ammonium hydroxide. A pipette was used to apply 1.6 ml of bleaching solution to the hair switch in a petri dish. The solution was then agitated for 90 seconds using the back of a plastic spoon spatula and the switch left for a further 20 minutes. Agitation for 1 minute with 1.6 ml of warm water was followed by rinsing under running warm water until the water ran clear and finally drying in air at room temperature.

Persulphate bleaching was performed using a freshly prepared commercially available bleaching paste. Three parts by volume persulphate bleach powder (Platin Eclair, L'Oreal) was mixed into a smooth paste with four parts by volume of 9% hydrogen peroxide (Igora Oxigenta Lotion, Schwarzkopf). The paste was liberally applied to the hair switch ensuring that all of the fibres were covered. After 20 minutes 5 ml of warm water was rubbed into the switch which was followed by rinsing under warm water until the water ran clear and finally drying in air at room temperature.

Transglutaminase (Tgase) Assay

Aliquots of 5 mg of dry human hair fibres were weighed out into screw-capped microfuge tubes. Cold putrescine solution without or with 20 mM cystamine (negative controls) was added to each sample and volume was made up to 100 μl of water to give putrescine concentrations twice that of the final desired concentration. One hundred μl of assay mixture containing 50 mM Tris.HCl pH 8.5, 5 mM $CaCl_2$, 10 mM DTT, 0.5% (w/v) Triton X-100 and 1 μCi/ml (0.4mM) [$^{14}$]-putrescine was added to each sample. The assay mixture was made up fresh each time from 1M stocks of Tris, $CaCl_2$ (both stored at room temperature) and DTT (stored at −20° C.) and 10% (w/v) TX-100 (stored at 4° C.). The final putrescine concentrations tested were 50, 100, 200, 500, 1000, 2000 and 4000 iM.

Samples were incubated at 37° C. for 1 hour and reactions stopped by the addition 20 μl of N, N-dimethylated casein (stock 30 mg/ml, stored at −20° C.) and 1 ml of 10% (w/v) trichloroacetic acid (TCA). The casein served to clump the fibres together once precipitated with acid and so reduce the loss of sample during washing.

Hair fibres were recovered by centrifugation at 13,000 rpm for 1 minute and the pellets washed three times in 1 ml of TCA for 20 min by shaking at 95° C. (total wash time=1 hr). The fibres were then solubilised by the addition of 1 ml of 90% soluene and incubation at 95° C. until complete dissolution had occurred (usually after about 10 min). After addition of 5 ml of Hionic-Fluor scintillation cocktail (Beckman) the tubes were placed into small scintillation vials and the incorporation of radioactive putrescine was measured in a Beckman LS 6000IC scintillation counter.

Dyeing of Hair Switches

Switches containing approximately 200 mg of fibre were treated with 0.5 ml of 2 mM Texas Red-Cadaverine (TRC) in 100 mM Tris pH8.5 either containing or lacking 10 mM DTT. The solution was massaged into the switches by hand in a petri dish and left to soak for 10 min. Switches were then rinsed with 100 ml of running water. The fibres were dried with paper towels and incubated at room temperature for 24 hr in a lidded petri dish containing some wetted tissue paper to maintain humidity. This procedure was carried out four times in succession to yield a total of four applications to each switch.

At the end of the experiment all fibre bundles were photographed to record the total level of colour change due to both dye penetration and incorporation. Permanent colour change was then visualised by boiling hair fibres in water to remove unincorporated dye. The switches were attached to paperclips using Araldite® adhesive and immersed in a beaker containing 500 ml of distilled water by hooking the clips over the edge of the flask. The water was brought to the boil with a Bunsen burner and the switches incubated for 20 minutes. Following this the water was replaced to remove excess dye and the procedure repeated twice more to give a total wash time in boiling water of 1 hour. Switches were dried and photographs were then taken of the final dried fibres to record the final permanent colour change.

Analysis of Colour Change

A Microscope Chromameter (Minolta CR-241) was used with a 0.3 mm diameter spot size. Samples of hair were mounted on a 1 cm wide strip of white double sided sticky tape which was attached to a microscope slide. In mounting the fibres care was taken to ensure that they were aligned and that the surface of the sticky tape was as evenly covered as possible. The sample positioning stage of the microscope was used to bring the hair fibres into focus and a measurement was taken. The sample was then randomly repositioned before the next measurement and a total of 10 measurements was taken. The colour of the undyed controls and the TGase dyed fibres was recorded in order to enable results to be displayed as the total colour change or AE value on the L*, a*, b* colour system.

Results

TGase Bleached Human Hair

In order to assess the effect of bleaching on the activity of. hair fibre TGase, blonde hair was subjected to both peroxide (less harsh) and persulphate (more harsh) treatments. The activity of the untreated and bleached hair was then assayed by the incorporation of radiolabelled putrescine. The activity of these samples was compared to a hair sample known to contain TGase activity that lies in the normal range. Surprisingly, bleach treatment of dyed hair appeared to stimulate the TGase activity and the degree of stimulation appeared to be correlated to the harshness of the treatment. Peroxide bleaching appeared to stimulate the enzyme activity by 40% relative to the untreated blonde hair while persulphate bleaching increased the activity by as much as 3.5-fold (Table 1).

TABLE 1

Transglutaminase (TGA) Activity of Blonde Hair samples

| Treatment | Relative TGA Activity |
| --- | --- |
| None | 100 |
| Peroxide | 140 |
| Persulphate | 360 |

Dyeing of Hair Switches

The extent of perceptible permanent colour change that could be conferred to blonde switches using a TGase substrate was determined. Four consecutive applications of 10 mM TRC were applied to the fibres for 10 minutes, each followed by rinsing, drying and incubating for 24 hours with and without 10 mM DTT (dithiothreitol reducing agent).

Quantitation of Colour Change

The extent of permanent colour change in these samples was determined using a tristimulus chromameter. The results are shown in Table 2.

TABLE 2

Total colour change (ΔE) of Treated Blonde Hair Samples

| Pre-treatment | Reducing Agent (DTT) | (ΔE) |
|---|---|---|
| None | None | 22.6 |
| None | 10 mM | 29.6 |
| Persulphate | None | 29.0 |
| Persulphate | 10 mM | 26.7 |

Thus, hair is dyed more effectively after pretreatment with oxidising agent, in the presence or absence of DTT reducing agent.

Example 2
Hair Bleaching Composition

An example of a hair bleaching composition is given below. The developer and base were stored in separate bottles before use. To use, the developer and base are mixed together. The composition is applied to hair and left for 20 minutes.

Developer

| Material | % Active Species | % w/t | Amount (g) |
|---|---|---|---|
| Lowenol 6559 (ex. Lowenstein) | 100 | 1.0 | 1.0 |
| Phosphoric Acid (ex Sigma) | 85 | 0.03 | 0.03 |
| Hydrogen Peroxide (ex. Fisher) | 35 | 17.1 | 17.1 |
| Polyquaterium 37 (ex Ciba) | 100 | 1.0 | 1.0 |
| Water (DI) | | | 80.87 |
| | | Total | 100.00 |

Base

| Material | % Active | % w/w | Amount (g) |
|---|---|---|---|
| EDTA (ex Sigma) | 100 | 0.6 | 0.6 |
| Sodium Sulphite (ex Fisher) | 100 | 1.0 | 1.0 |
| Sodium Isoascorbate (ex Lowenstein) | 100 | 0.15 | 0.15 |
| Propylene Glycol (ex Sigma) | 100 | 8.4 | 8.4 |
| Lowenol C-243 (ex Lowenstein) | 100 | 8.0 | 8.0 |
| Lowenol S-216X (ex Lowenstein) | 100 | 22.2 | 22.2 |
| Oleic Acid (ex Aldrich) | 100 | 8.6 | 8.6 |
| Isopropanol (ex Sigma) | 100 | 12.5 | 12.5 |
| Texas Red-cadaverine (ex Molecular Probes) | 100 | 0.3 | 0.3 |
| Ammonia (ex Sigma) | 28 | 33 | 33 |
| Water (DI) | | | 5.25 |
| | | Total | 100.00 |

Example 3
Hair Colouring Composition

A hair colouring composition is formulated as set out below. The developer and base are stored in separate bottles before use. To use, the developer and base are mixed together to form a hair colouring composition according to the present invention, having a pH greater than pH10. The composition is applied to hair and left for 20 minutes.

| Material | % AD | % w/w | Amount (g) |
|---|---|---|---|
| Developer | | | |
| Lowenol 6559 (ex Lowenstein) | 100 | 1.0 | 1.0 |
| Phosphoric Acid (ex Sigma) | 85 | 0.03 | 0.03 |
| Hydrogen Peroxide (ex Fisher) | 35 | 17.1 | 17.1 |
| Polyquaterium 37 (ex Ciba) | 100 | 1.0 | 1.0 |
| Water (DI) | | | 80.87 |
| | | Total | 100.00 |
| Dye Base | | | |
| EDTA (ex Sigma) | 100 | 0.6 | 0.6 |
| Sodium Sulphite (ex Fisher) | 100 | 1.0 | 1.0 |
| Sodium Isoascorbate (ex Lowenstein) | 100 | 0.15 | 0.15 |
| Propylene Glycol (ex Sigma) | 100 | 8.4 | 8.4 |
| Lowenol C-243 (ex Lowenstein) | 100 | 8.0 | 8.0 |
| Lowenol S-216X (ex Lowenstein) | 100 | 22.2 | 22.2 |
| Oleic acid (ex Aldrich) | 100 | 8.6 | 8.6 |
| Isopropanol (ex Sigma) | 100 | 12.5 | 12.5 |
| Texas Red-cadaverine (ex Mol Probes) | 100 | 0.3 | 0.3 |
| Ammonia (ex Sigma) | 28 | 33.0 | 33.0 |
| RODOL DJ p-phenylene-diamine (Primary Intermediate) (ex Lowenstein) | 100 | 1.0 | 1.0 |
| RODOL RS resonanol (Coupler) (ex Lowenstein) | 100 | 1.0 3.25 | 1.0 3.25 |
| Water (DI) | | qv | qv |
| | | Total | 100.00 |

What is claimed is:

1. A method of colouring hair comprising the step of applying to the hair a composition comprising: a compound which is capable of acting as a substrate for endogenous transglutaminase in and/or on hair and which comprises a chromophore that is capable of absorbing and/or emitting light in the visible part of the electromagnetic spectrum; and a reducing agent comprising one or more thiol group, wherein the said compound forms a covalent bond to the hair by the action of the endogenous transglutaminase.

2. A method as claimed in claim 1, wherein the compound comprises an amino group covalently bonded to the chromophore.

3. A method as claimed in claim 1, wherein the compound comprises a group of formula $NH_2$ covalently bonded to the chromophore by a linker group of formula $(CH_2)_n$, wherein n is an integer from 1 to 6.

4. A method as claimed in claim 1, wherein the compound is in solution and is present in the composition at a concentration of from 0.0001M to 0.01M.

5. A method as claimed in claim 1, wherein the reducing agent comprises dithiothreitol, thioglycolate or a mixture thereof.

6. A method as claimed in claim 1, wherein the reducing agent is in solution and is present in the composition in an amount such that the molar ratio of the reducing agent to the compound is in the range of from 10:1 to 1:1.

7. A method as claimed in claim 1 which has a pH of from 7.5 to 9.5.

8. A method as claimed in claims 7 which has a pH of from 8 to 9.

9. A method as claimed in claim 1, wherein the chromophore is an organic dye.

10. A method as claimed in claim 9, wherein the dye colours hair red.

11. A method as claimed in claim 1, in which the composition further comprises a fragrance or perfume.

12. A method as claimed in claim 1, in which the composition further comprises one or more surfactants.

13. A method as claimed in claim 1, in which the composition further comprises calcium ions.

14. A method as claimed in claim 1, in which the composition further comprises a hair penetration agent.

15. A method as claimed in claim 1, in which the composition further comprises a cosmetically acceptable diluent or carrier.

* * * * *